(12) United States Patent
Dey et al.

(10) Patent No.: US 9,964,552 B2
(45) Date of Patent: May 8, 2018

(54) MASS SPECTROMETRIC IDENTIFICATION AND/OR QUANTITATION OF CATECHOLAMINES USING AMINOPYRAZOLES

(71) Applicant: DH Technologies Development PTE Ltd., Singapore (SG)

(72) Inventors: Subhakar Dey, Lexington, MA (US); Subhasish Purkayastha, Acton, MA (US)

(73) Assignee: DH Technologies Development Pte. Ltd., Singapore (SG)

( * ) Notice: Subject to any disclaimer, the term of this patent is extended or adjusted under 35 U.S.C. 154(b) by 0 days. days.

(21) Appl. No.: 15/032,121

(22) PCT Filed: Oct. 22, 2014

(86) PCT No.: PCT/IB2014/002198
§ 371 (c)(1),
(2) Date: Apr. 26, 2016

(87) PCT Pub. No.: WO2015/063563
PCT Pub. Date: May 7, 2015

(65) Prior Publication Data
US 2016/0305969 A1    Oct. 20, 2016

Related U.S. Application Data

(60) Provisional application No. 61/897,683, filed on Oct. 30, 2013.

(51) Int. Cl.
*G01N 24/00* (2006.01)
*G01N 33/94* (2006.01)
(Continued)

(52) U.S. Cl.
CPC ....... *G01N 33/9406* (2013.01); *C07B 59/001* (2013.01); *C07B 59/002* (2013.01);
(Continued)

(58) Field of Classification Search
CPC .. G01N 33/9406; G01N 33/00; C07B 59/001; C07B 59/002; C07C 251/22; C07D 231/46
(Continued)

(56) References Cited

U.S. PATENT DOCUMENTS

2006/0102836 A1    5/2006  Iida et al.
2006/0292039 A1   12/2006  Iida
(Continued)

FOREIGN PATENT DOCUMENTS

| JP | 2003057244 A | 2/2003 |
| WO | 2005027725 A2 | 3/2005 |
| WO | 2006015606 A1 | 2/2006 |

OTHER PUBLICATIONS

International Search Report and Written Opinion for PCT/IB2014/002198 dated Feb. 16, 2015.

*Primary Examiner* — Brian J. Sines

(57) ABSTRACT

A method is described for mass spectrometric analysis, detection and quantification of catecholamines. The methods can comprise reacting the catecholamines with a 4-amino-antipyrine reagent and detecting and/or quantifying the adduct produced by the reaction. The methods can also allow for multiplexing. Compounds formed by the reactions are also provided.

8 Claims, 2 Drawing Sheets

(51) Int. Cl.
*C07B 59/00* (2006.01)
*C07C 251/22* (2006.01)
*C07D 231/46* (2006.01)

(52) U.S. Cl.
CPC .......... *C07C 251/22* (2013.01); *C07D 231/46* (2013.01); *C07B 2200/05* (2013.01); *C07C 2601/16* (2017.05); *G01N 2560/00* (2013.01)

(58) Field of Classification Search
USPC .............. 436/43, 91, 98, 164, 171, 172, 173
See application file for complete search history.

(56) References Cited

U.S. PATENT DOCUMENTS

2009/0176312 A1* 7/2009 Selinfreund .............. B01L 7/52
  436/164
2010/0148055 A1* 6/2010 Caulfield ........... G01N 33/9406
  250/282

* cited by examiner

MASS SPECTROMETRIC IDENTIFICATION AND/OR QUANTITATION OF CATECHOLAMINES USING AMINOPYRAZOLES

RELATED APPLICATIONS

This application claims the benefit of U.S. Patent Application Ser. No. 61/897,683, filed Oct. 30, 2013, the content of which is incorporated by reference herein in its entirety.

FIELD

The present teachings relate to the fields of mass spectrometry and reagents useful for mass spectrometry.

INTRODUCTION

Labeling chemistry is generally used to improve a mass spectrometry signal.

Catecholamines are molecules that have a catechol nucleus consisting of benzene with two hydroxyl side groups and a side-chain amine. In the human body, the most abundant catecholamines are epinephrine (adrenaline), norepinephrine (noradrenaline) and dopamine. Catecholamines are water-soluble and are 50% bound to plasma proteins, so they circulate in the bloodstream The accurate analysis and quantification of these molecules is becoming increasingly important. However, a need still exists for labels for improved mass spectrometry analysis of these compounds because the analysis of these compounds by mass spectrometry has conventionally been difficult. For example, many of these compounds do not contain ionizable groups. Thus, the quantitation of these molecules, especially at low concentrations, can be difficult.

A need exists for a method of quantitating these analytes that overcomes these previous difficulties.

SUMMARY

In some embodiments, methods of detecting the presence of one or more catecholamines in a sample are provided. In some embodiments, the method comprises a) reacting the sample with a 4-aminoantipyrine reagent, or a heavy atom derivative thereof, under conditions sufficient to react with a catecholamine, if any, present in the sample to form a 4-aminoantipyrine-reagent-catecholamine adduct, or a heavy atom derivative thereof; b) obtaining a mass spectrum of said reacted sample; and c) analyzing the mass spectrum to determine whether the sample contains a 4-aminoantipyrine-reagent-catecholamine adduct or an ionic fragment thereof.

In some embodiments, compounds of Formula I or a heavy atom derivative thereof:

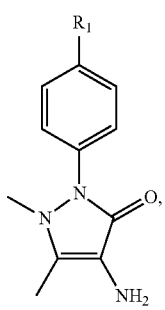

I wherein
$R_1$ is H or

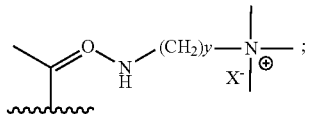

$y$ is 1-6; and
X is halogen are provided.

In some embodiments, compounds of Formula II or a heavy atom derivative thereof:

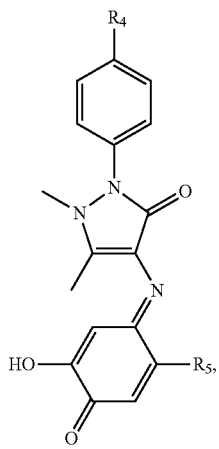

II wherein
$R_4$ is H or

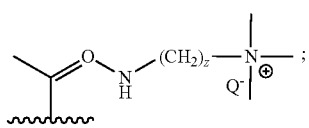

$R_5$ is

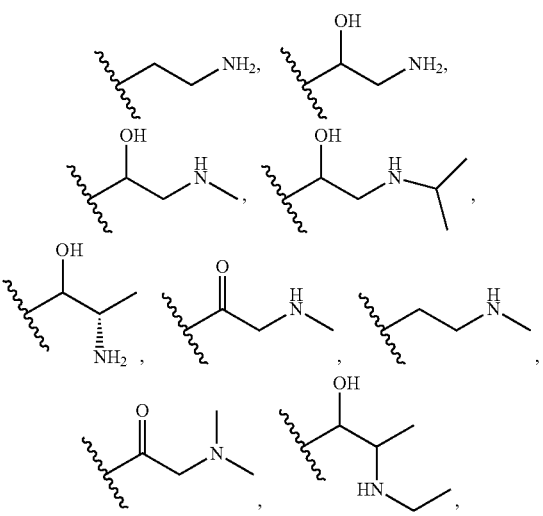

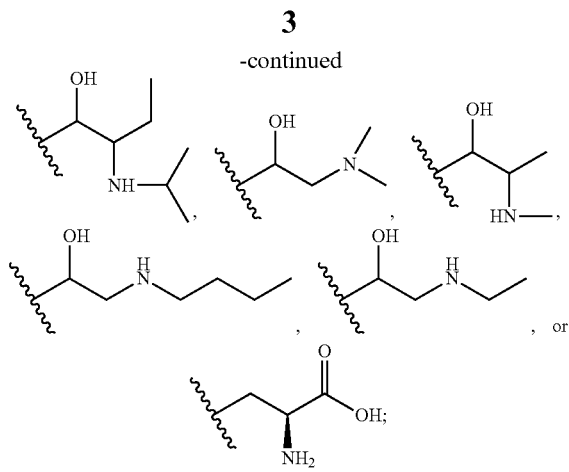

z is 1-6; and
Q is a halogen are provided.

In some embodiments, compounds of Formula III or a heavy atom derivative thereof:

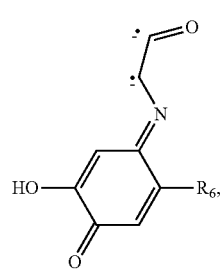

III wherein
$R^6$ is

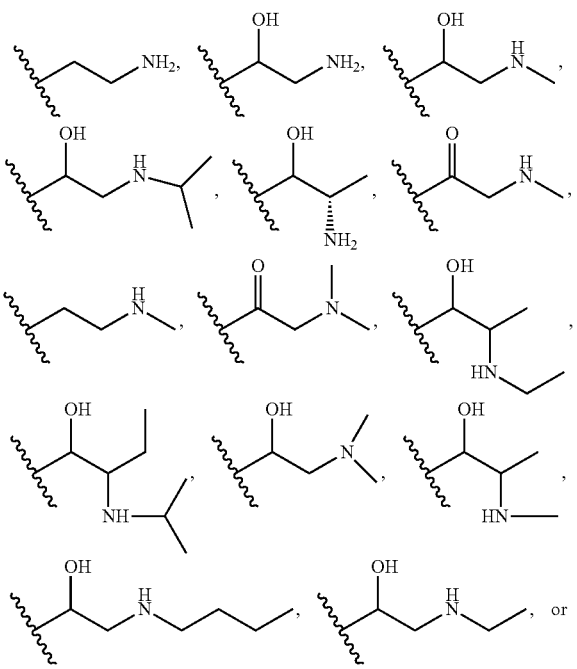

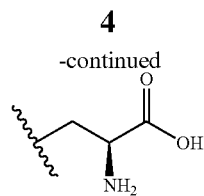

are provided.

In some embodiments methods of making a compound of Formula II

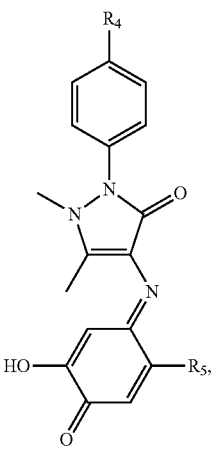

II the method comprising reacting

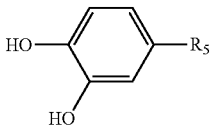

with a 4-aminoantipyrine regent under conditions sufficient to produce a compound of Formula II,
wherein
$R_4$ is H or

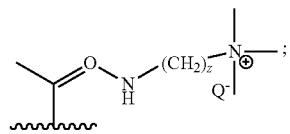

$R_5$ is

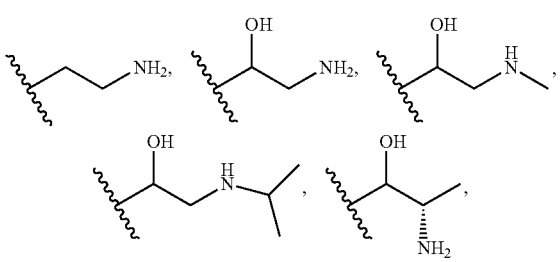

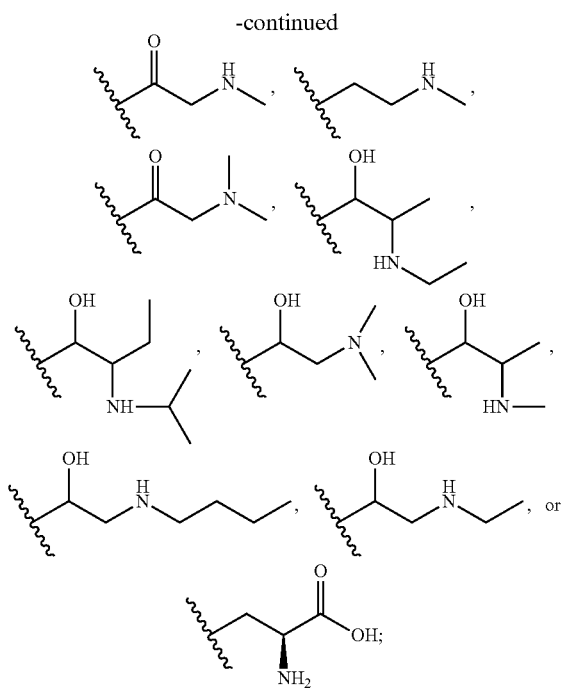

z is 1-6; and

Q is a halogen are provided.

In some embodiments, kits are provided. In some embodiments, the kit comprises a 4-aminoantipyrine reagent, one or more analyte standards, one or more internal standards, one or more sample preparation cartridges and plates, a biological matrix, a solvent, tubes, a HPLC columns, and one or more liquid chromatography buffers.

BRIEF DESCRIPTION OF THE DRAWINGS

The present teachings will be more fully understood with reference to the appended drawings. The drawings are intended to illustrate, not limit, the present teachings.

Figure 1:
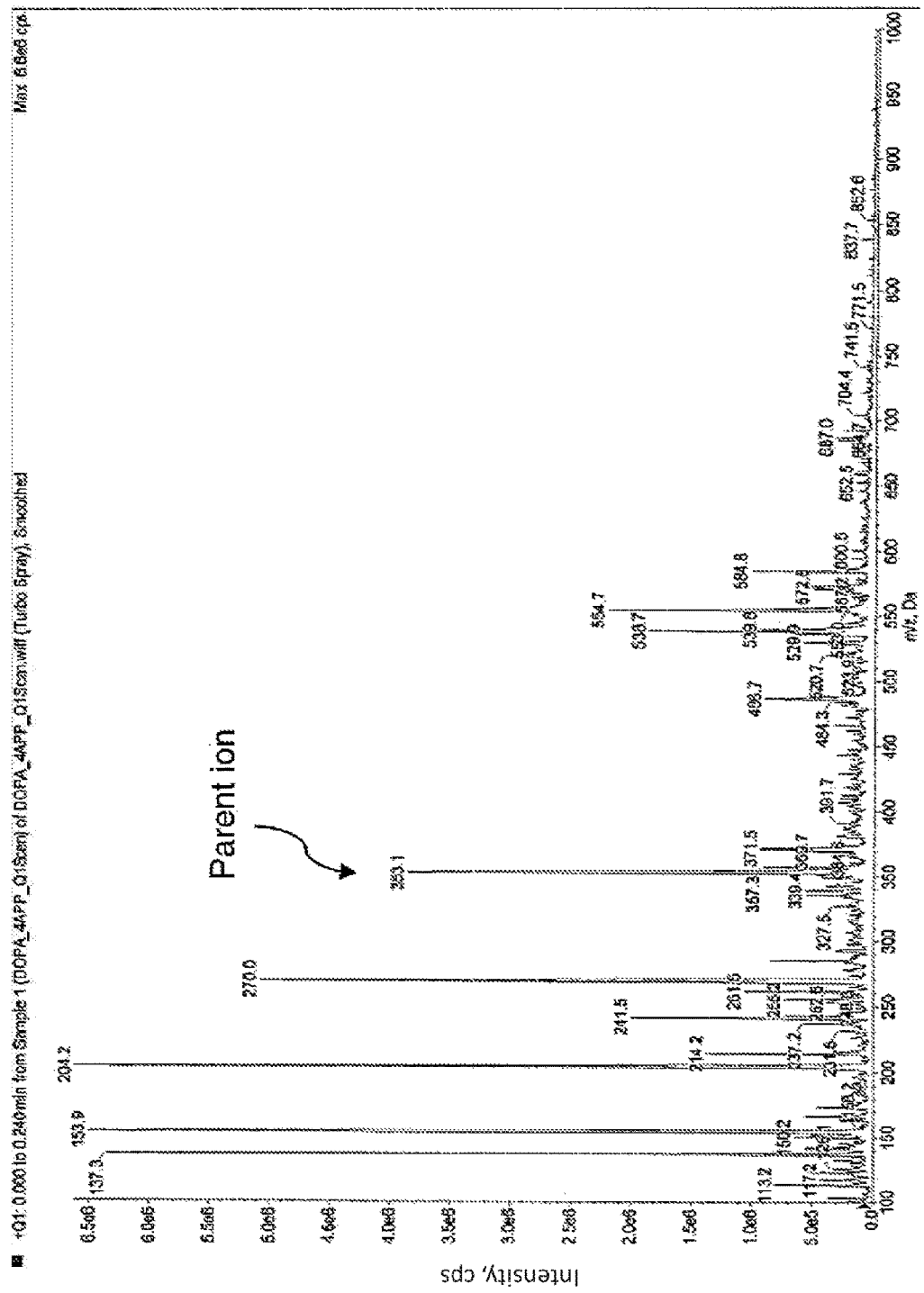
FIG. 1 shows the Q-1 MS scan of the 4-AAP-dopamine adduct, parent ion, that was generated according to Example 1.

A detailed description of various embodiments is provided herein below with reference, by way of example, to the following drawings. It will be understood that the drawings are exemplary only and that all reference to the drawings is made for the purpose of illustration only, and is not intended to limit the scope of the embodiments described herein below in any way. For convenience, reference numerals may also be repeated (with or without an offset) throughout the figures to indicate analogous components or features.

DETAILED DESCRIPTION OF VARIOUS EMBODIMENTS

It will be appreciated that for clarity, the following discussion will explicate various aspects of embodiments of the applicants' teachings, but omitting certain specific details wherever convenient or appropriate to do so. For example, discussion of like or analogous features in alternative embodiments may be somewhat abbreviated. Well-known ideas or concepts may also for brevity not be discussed in any great detail. The skilled person will recognize that some embodiments may not require certain of the specifically described details in every implementation, which are set forth herein only to provide a thorough understanding of the embodiments. Similarly it will be apparent that the described embodiments may be susceptible to slight alteration or variation according to common general knowledge without departing from the scope of the disclosure. Aspects of the applicants' teachings may be further understood in light of the following examples and description of various embodiments, which should not be construed as limiting the scope of the applicants' teachings in any way.

According to some embodiments, methods of detecting the presence of, and/or quantifying, one or more catecholamines in a sample is provided. Examples of catecholamines that be detected and/or quantified include, but are not limited to those shown in Table 1.

TABLE 1

| Catecholamines | | |
|---|---|---|
| Catechol-amine | Structure | CAS Number |
| Iso-prenaline | | 51-31-0 |
| Norepine-phrine | | 51-41-2 |
| Nordefrin | | 6539-57-7 |
| Adrenalone hydro-chloride | | 62-13-5 |
| Epinine hydro-chloride | | 62-32-8 |
| 2-(dimethyl-amino)-3',4'-dihydroxy-(8CI); 2-(Dimethyl-amino)-3',4'-dihydroxy-aceto-phenone | | 150-10-7 |

TABLE 1-continued

Catecholamines

| Catechol-amine | Structure | CAS Number |
|---|---|---|
| Dioxethe-drin | 4-(1-hydroxy-2-(ethylamino)propyl)benzene-1,2-diol | 497-75-6 |
| Ety-prenaline | 4-(1-hydroxy-2-(isopropylamino)butyl)benzene-1,2-diol | 530-08-5 |
| N-Methyl-epinephrine | 4-(1-hydroxy-2-(dimethylamino)ethyl)benzene-1,2-diol | 554-99-4 |
| Dihydroxy-ephedrine hydro-chloride | 4-(1-hydroxy-2-(methylamino)propyl)benzene-1,2-diol · HCl | 946-43-0 |
| Butylnor-adrenaline | 4-(1-hydroxy-2-(butylamino)ethyl)benzene-1,2-diol | 1951-20-8 |
| Ethylnor-adrenaline | 4-(1-hydroxy-2-(ethylamino)ethyl)benzene-1,2-diol | 2947-00-4 |
| Dopa, 3,4-Dihydroxy-phenyl-alanine | 2-amino-3-(3,4-dihydroxyphenyl)propanoic acid | 59-92-7 |
| Dopamine | 4-(2-aminoethyl)benzene-1,2-diol | 51-61-6 |

In some embodiments, the one or more catecholamines detected and/or quantified is selected from the group of Table 1. In some embodiments, the catecholamine detected and/or quantified is epinephrine, norepinephrine, dopamine, or a salt or hydrates thereof, or any combination thereof. In some embodiments, the one or more catecholamines is epinephrine, isoprenaline, norepinephrine, nordefrin, adrenalone hydrochloride, epinine hydrochloride, 2-(dimethylamino)-3',4'-dihydroxy-(8Cl), 2-(Dimethylamino)-3',4'-dihydroxyacetophenone, dioxethedrin, etyprenaline, N-methylepinephrine, dihydroxyephedrine hydrochloride, butylnoradrenaline, ethylnoradrenaline, 3,4-dihydroxy-phenylalanine, dopamine, or a salt or hydrates thereof, or any combination thereof.

In some embodiments, the method comprises a) reacting a sample with a 4-aminoantipyrine (4-AAP) reagent, or a heavy atom derivative thereof, under conditions sufficient to react with a catecholamine, if any, present in the sample to form a 4-aminoantipyrine-reagent-catecholamine adduct, or a heavy atom derivative thereof; b) obtaining a mass spectrum of said reacted sample; and c) analyzing the mass spectrum to determine whether the sample contains a 4-aminoantipyrine-reagent-catecholamine adduct or an ionic fragment thereof. The mass spectrum analysis will indicate whether the adduct or the ionic fragment thereof is present. If the adduct or fragment thereof is present in the mass spectrum, then the presence of the adduct or ionic fragment thereof indicates that the catecholamine is also present in the sample.

In some embodiments, the analyzing step comprises detecting one of more mass signals associated with any of said adduct and one or more fragments thereof. The detection of mass signals can be used with any standard mass spectrometer, such as, but not limited to, an QTRAP® 5500 mass-spectrometer. The mass spectrometer can be used in direct infusion mode. The specific mass-spectrometer and mode of operation is not critical so the machine and variables of using the machine can be modified depending upon the user's preferences.

In some embodiments, the method comprises quantitating the amount of the catecholamine in the sample. The quantitating can be done, for example, by comparing the mass spectra to a standard. The standard can be an internal standard or an analyte standard. For example, heavy atom labeled analytes can be used. The heavy atom labeled analytes can be heavy atom labeled catecholamines, such as the catecholamines described herein.

As used herein, the term "heavy atom" refers to a molecule that has one or more atoms substituted with a heavier atom. For example, a hydrogen can be substituted with a deuterium. A $^{12}C$ carbon can be substituted with a $^{13}C$ carbon. Where a molecule has more than one hydrogen, one or more, or all, of the hydrogens can be substituted with a heavier hydrogen atom. Where a molecule has more than one carbon, one or more, or all, of the carbons can be substituted with a heavier carbon atom.

Examples of heavy atom labeled analytes that can be used as standards include, but are not limited to:

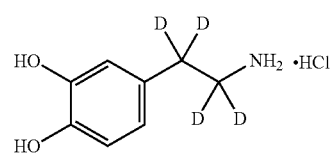 [SMILES: [2H]C([2H])(N)C([2H])([2H])c1ccc(O)c(O)c1 ; Cl]

(Dopamine-1,1,2,2-d4 hydrochloride),

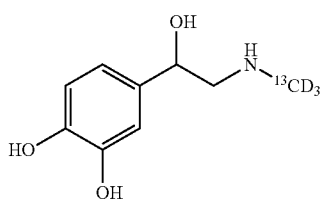

(Epinephrine (methyl-13C,d3), and

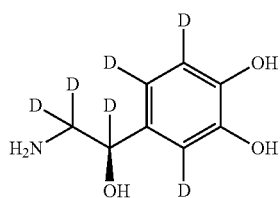

(Norepinephrine-2,5,6,α,β,β-d6). These are non-limiting examples and other heavy atom analytes can also be used.

In some embodiments, the 4-aminoantipyrine reagent is a compound of Formula I or a heavy atom derivative thereof:

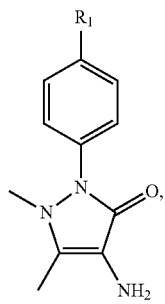

I wherein $R_1$ is H or

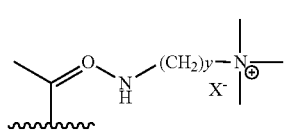

y is 1-6; and $X^-$ is an anion.

As used herein, when the term "heavy atom derivative thereof" refers to a compound, the term means that one or more of the carbons in the compound are substituted with $^{13}C$ carbon. In some embodiments, all of the carbons are substituted. The substitution can be used to facilitate the analysis, detection, and/or quantification of the catecholamines in the sample.

In some embodiments, the heavy atom derivative of Formula I is a compound of Formula Ia, Ib, or Ic.

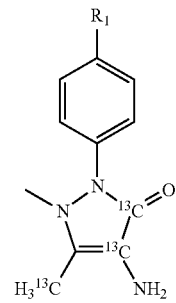

Ia

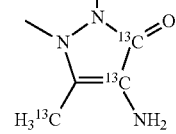

Ib

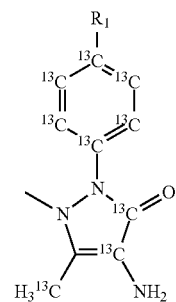

Ic

In some embodiments of the compound of Formula I, Ia, Ib, or Ic, $R_1$ is H. In some embodiments, $R_1$ is

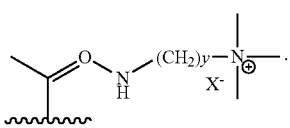

In some embodiments of the compound of Formula I, Ia, Ib, or Ic, X is Cl, F, I, or Br. In some embodiments, X is Br.

In some embodiments, the method produces a aminoantipyrine-catecholamine adduct compound of Formula II, or a heavy atom derivative thereof:

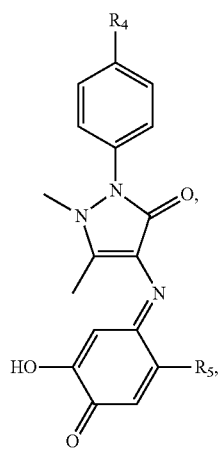

wherein
R₄ is H or

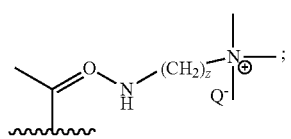

R₅ is

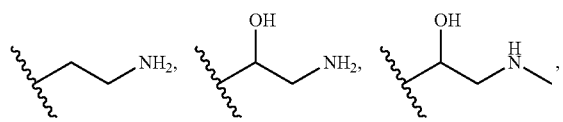

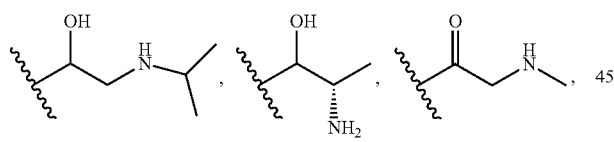

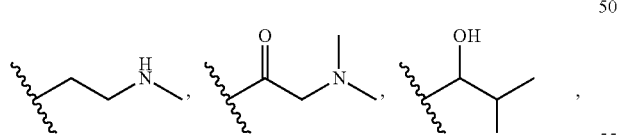

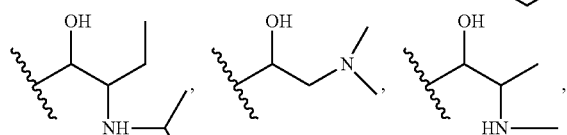

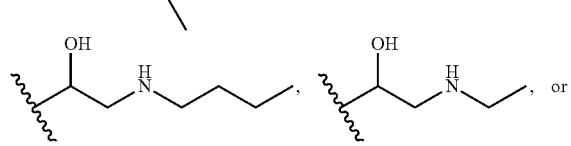, or z is 1-6; and

Q is a halogen. As is evident to one of skill in the art, the various R5 groups are specific to the different exemplary catecholamines that can be detected and quantified according to the methods described herein. The side chains can also be seen in Table 1.

In some embodiments, the heavy atom derivative of Formula II is a compound of Formula IIa or IIb In some embodiments of the compound of Formula II, IIa, or IIb, R₄ is

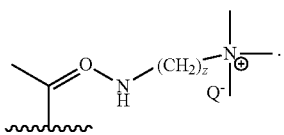

In some embodiments, R4 is H.

In some embodiments of the compound of Formula II, IIa, or IIb, z is 3.

In some embodiments of the compound of Formula II, IIa, or IIb, z is 3.

In some embodiments of the compound of Formula II, IIa, or IIb, Q is Cl, F, I, or Br. In some embodiments, Q is Br.

In some embodiments, the method generates an ionic fragment of the aminoantipyrine-catecholamine adduct. In some embodiments, the ionic fragment is detected and/or used for quantifying the amount of the catecholamine in the sample. In some embodiments, the ionic fragment is a compound of Formula III, or a heavy atom derivative thereof:

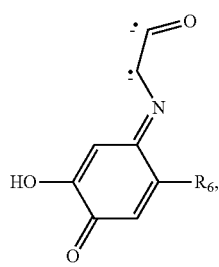

III wherein $R_6$ is

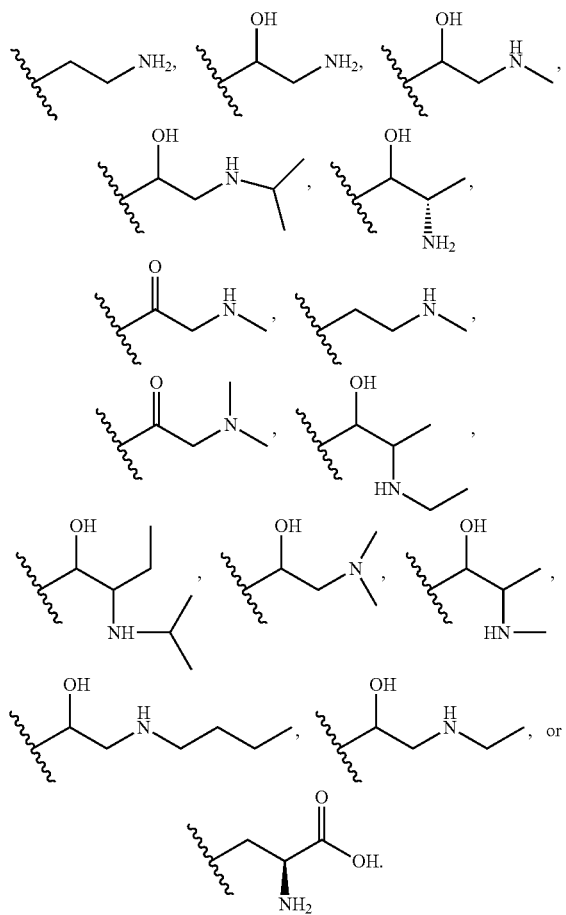

, or

As is evident to one of skill in the art, the various R6 groups are specific to the different exemplary catecholamines that can be detected and quantified according to the methods described herein. The side chains can also be seen in Table 1.

In some embodiments, the sample is reacted with the 4-aminoantipyrine reagent under conditions to form a 4-aminoantipyrine-catecholamine adduct if the catecholamine is present. In some embodiments, the method comprises contacting the sample with 4-aminoantipyrine reagent in the presence of ammonium bicarbonate (i.e., buffer) and $K_2[Fe(CN)_6]$ (i.e. oxidizing agent) to produce the 4-aminoantipyrine-catecholamine adduct. In some embodiments, the catecholamine is in the form of hydrochloride salt. In some embodiments, the ammonium bicarbonate is a buffer. In some embodiments, the buffer is at a pH of about pH 8-9. The components can be mixed together and allowed to react for 5-30, 5-20, or 5-15 minutes. In some embodiments, the mixture is allowed to react for at least, or about, 5, 10, 15, or 20 minutes. In some embodiments, the mixture is allowed to react for less than 20 minutes. The mixture can also be filtered prior to being analyzed on a mass spectrometer. Examples of a filter is, but not limited to a C18 (500 mg) cartridge. Other buffers, such as, but not limited to, phosphate buffers can also be used. The pH range of the buffers can be about 8 to about 11. Examples of other oxidizing agents include, but are not limited to, hydrogen peroxide, copper sulfate or sodium persulfate. Any suitable oxidizing agent can be used so long as the oxidizing agent can will facilitate the reaction of the 4-aminoantipyrine reagent and the catecholamine, if the catecholamine is present in the sample.

As used herein, the term "sample" refers to sample that may or may not contain the catecholamine. In some embodiments, the sample is known to contain a catecholamine. In some embodiments, the sample is expected to contain a catecholamine. The "sample" can be also be referred to as a "test sample."

According to some embodiments, a compound of Formula I or a heavy atom derivative thereof:

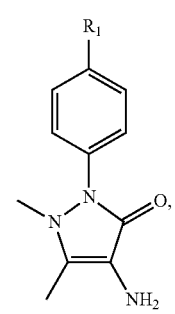

I wherein
$R_1$ is H or

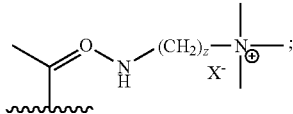

y is 1-6; and

X is halogen is provided.

In some embodiments, the heavy atom derivative of Formula I is a compound of Formula Ia, Ib, or Ic.

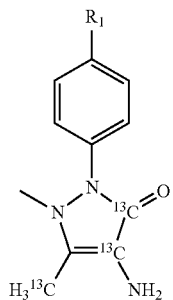

Ia

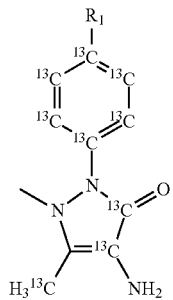

Ib

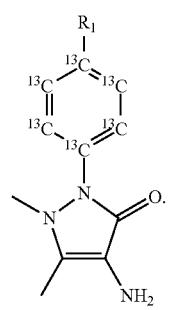

Ic

In some embodiments of a compound of Formula I, Ia, Ib, or Ic, $R_1$ is

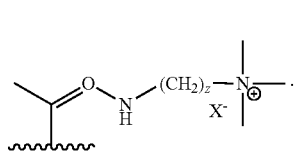

In some embodiments, $R_1$ is H.

In some embodiments of a compound of Formula I, Ia, Ib, or Ic, y is 3.

In some embodiments of a compound of Formula I, Ia, Ib, or Ic, X is Cl, I, F, or Br. In some embodiments, X is Br.

According to some embodiments, a compound of Formula II, or a heavy atom derivative thereof:

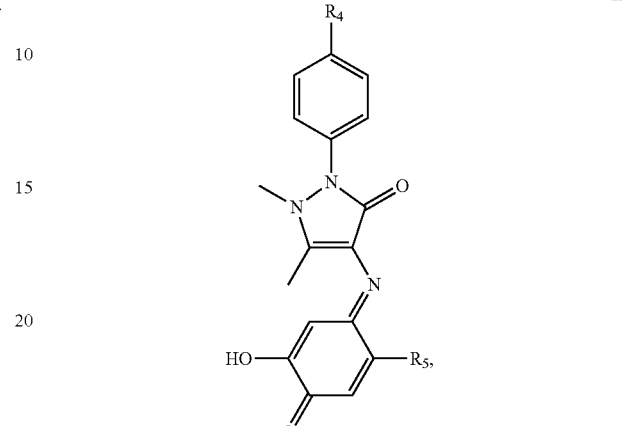

II wherein $R_4$ is H or

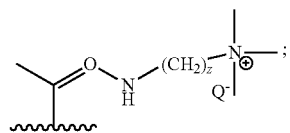

$R_5$ is

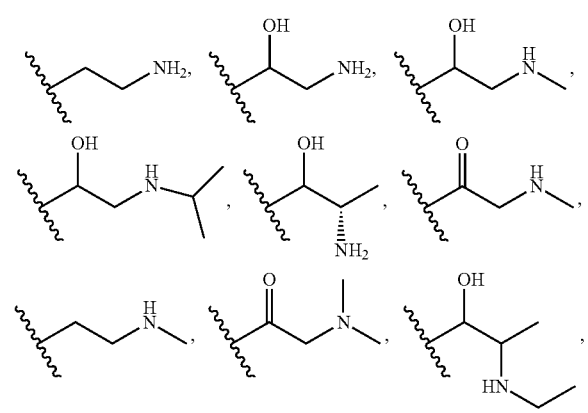

-continued

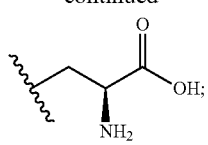

z is 1-6; and

Q is a halogen is provided.

In some embodiments, the heavy atom derivative of Formula II is a compound of Formula IIa or IIb

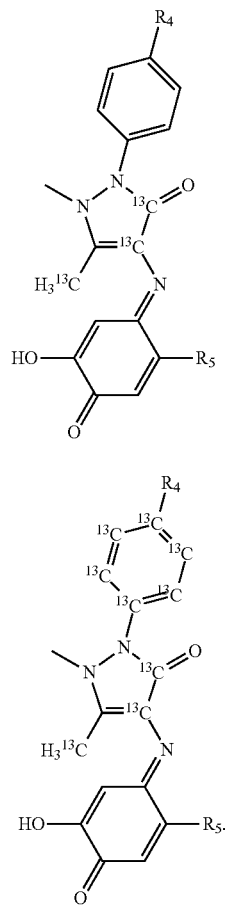

IIa

IIb

In some embodiments of a compound of Formula II, IIa, or IIb, or Ic, $R_4$ is

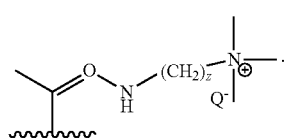

In some embodiments, $R_4$ is H.

In some embodiments of a compound of Formula II, IIa, or IIb, or Ic, z is 3. In some embodiments, Q is F, I, Cl, or Br. In some embodiments, Q is Br.

According to some embodiments, a compound of Formula III, or a heavy atom derivative thereof:

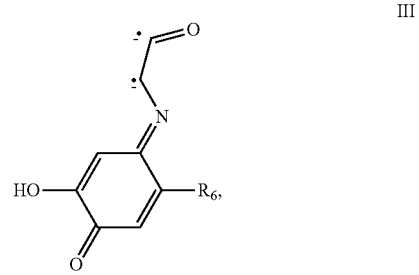

III wherein $R_6$ is

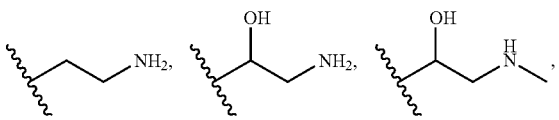

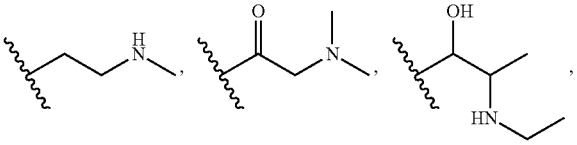

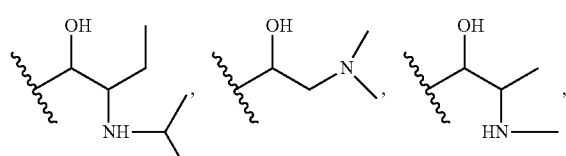

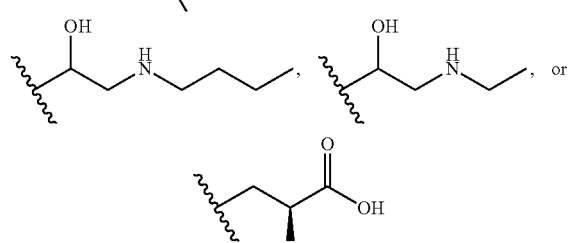

is provided. In some embodiments, the heavy atom derivative is a compound of Formula IIIa

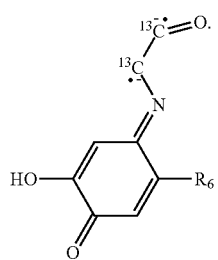
In some embodiments, methods of making a compound of Formula II
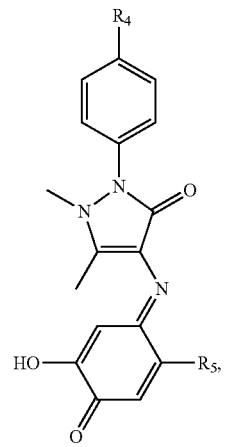
wherein
R₄ is H or
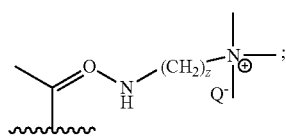
R₅ is
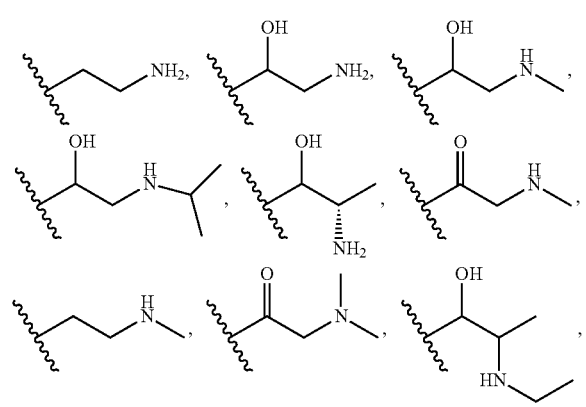
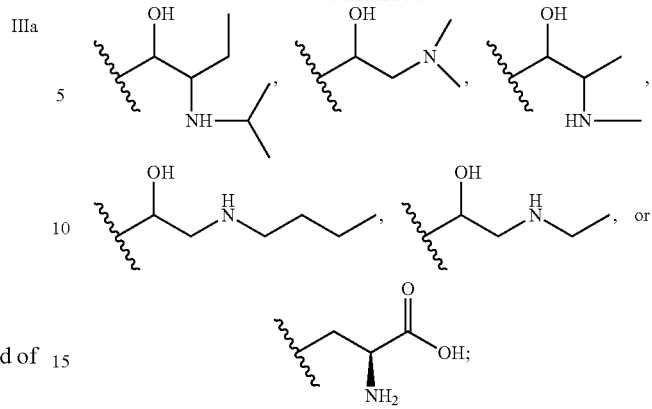
z is 1-6; and
Q is a halogen is provided.
In some embodiments, the method comprises reacting
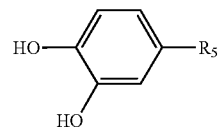
with a 4-aminoantipyrine regent under conditions sufficient to produce a compound of Formula II, wherein
R₄ is H or
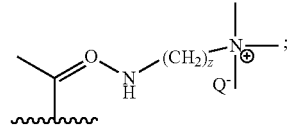
R₅ is
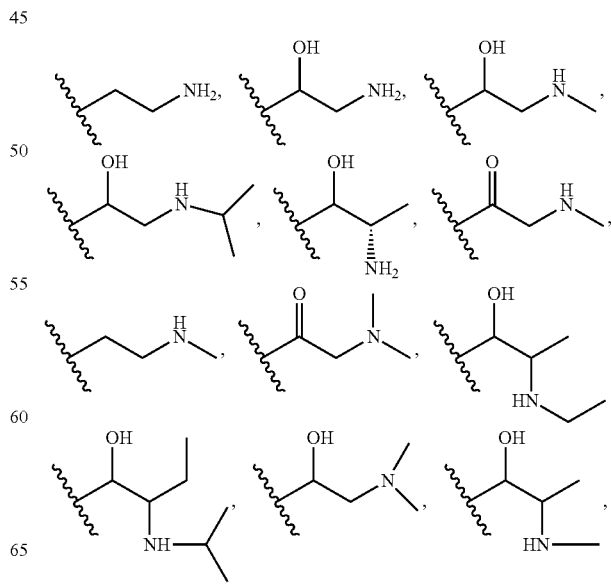

-continued

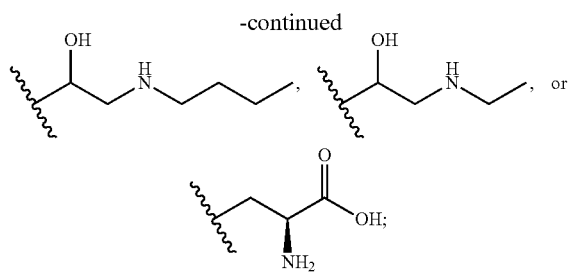

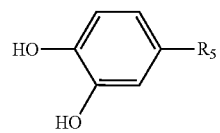

z is 1-6; and
Q is a halogen.

In some embodiments, the method comprises reacting

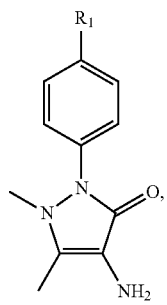

(i.e., the catecholamine) with a 4-aminoantipyrine reagent in the presence of a buffer and an oxidizing agent to produce a compound of Formula II. In some embodiments, the buffer is at a pH of about 8 to about 11. In some embodiments, the buffer is an ammonium bicarbonate buffer. In some embodiments, the buffer is a phosphate buffer. In some embodiments, the oxidizing agent is $K_2[Fe(CN)_6]$. In some embodiments, the oxidizing agent is hydrogen peroxide, copper sulfate or sodium persulfate. As discussed herein, the specific buffer and oxidizing agent is not specific so long as it allows the catecholamine and the 4-aminoantipyrine reagent to react with one another to form a compound of Formula II.

In some embodiments, the 4-aminoantipyrine reagent is a compound of Formula I or a heavy atom derivative thereof:

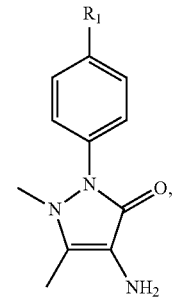

wherein
$R_1$ is H or

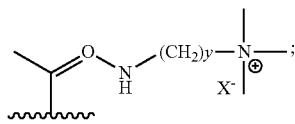

y is 1-6; and
X is halogen.

According to some embodiments, kits are also provided. In some embodiments, the kit comprises a 4-aminoantipyrine reagent, such as but not limited to those described herein, one or more analyte standards, one or more internal standards, one or more sample preparation cartridges and plates, a biological matrix, a solvent, tubes, a HPLC columns, and one or more liquid chromatography buffers. In some embodiments, the 4-aminoantipyrine reagent is a compound of Formula I or a heavy atom derivative thereof:

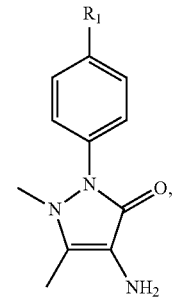

wherein
$R_1$ is H or

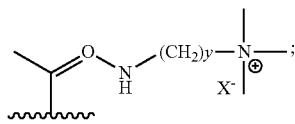

y is 1-6; and
X is halogen.

According to various embodiments, the kit can comprise buffers, one or more chromatographic columns, and optionally other reagents and/or components useful in carrying out the methods or assay. In some embodiments, the kit can comprise, for example, a homogeneous assay such that the user need only add a sample. In some embodiments, the kit can comprise calibration or normalization reagents or standards. Information pertaining to instrument settings that can or should be used to perform an assay can also be included in the kit. In some embodiments, information pertaining to sample preparation, operating conditions, volumetric amounts, temperature settings, and the like, is included with the kit. The kit can also be packaged in a hermetically sealed container containing one or more reagent vessels and appropriate instructions. An electronic medium can be included in the kit, having stored thereon electronic information pertaining to one or more assays, measurement values, transition pairs, operating instructions, software for carrying out operations, a combination thereof, or the like. According to various embodiments, a method can be provided for the synthesis of the 4-aminoantipyrine reagent and its intermediates. In some embodiments, the kit can comprise at least one standard comprising a known concentration of a known catecholamine analyte. According to some embodiments, kit can comprise instructions for labeling, quantifying, and detecting the catecholamine analyte.

As discussed herein, the method can further comprise providing a standard comprising a known catecholamine. The internal standards can be used to both detect and quantify the amount of a catecholamine in the same mass spectrum analysis. For example, two different labeled internal standards and reagents can be used to label samples according to the methods described herein. "Labeling" a sample refers to the formation of the adduct. That is, the catecholamine, if present, is labeled with the 4-aminoantipyrine reagent. After labeling, the samples can be mixed and analyzed by, for example, LC/MS/MS to obtain the quantitation information of the analyte present in two different samples. A non-limiting example of this method is as follows:

Sample 1+Internal Standard 1→sample preparation→label with reagent 1

Sample 2+Internal Standard 2→sample preparation→label with reagent 2

Mix above reactions and analyzed. This is an example of duplex, which can be extended to any other multiplex format.

If, for example, the samples contained dopamine, internal standard 1 can be:

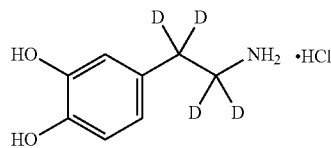 [SMILES: [2H]C([2H])(N)C([2H])([2H])c1ccc(O)c(O)c1 ; Cl]

Dopamine-1,1,2,2-d4 hydrochloride, and internal standard 2 can be:

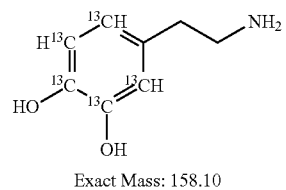 [SMILES: NCCc1[13cH][13cH][13c](O)[13c](O)[13cH]1]

Exact Mass: 158.10

Dopamine 13C6. The first 4-aminoantipyrine reagent (Reagent 1) can be

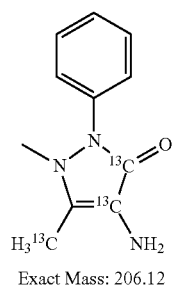

Exact Mass: 206.12 and the second 4-aminoantipyrine reagent (Reagent 2 can be

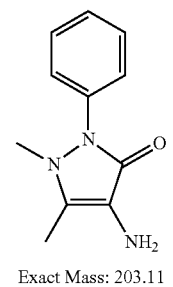

Exact Mass: 203.11

By using different internal standards and different reagents, this allows for the mixtures of samples to determine the presence or absence of the catecholamine in different samples, as well as the ability to quantify and detect in the same or different samples at the same time. This provides the unexpected advantage of simultaneous analysis of many samples and, thus, an increase in throughput.

In some embodiments, a relative concentration of the catecholamine analyte can be obtained. In other embodiments, absolute quantitation of the catecholamine analyte can be obtained by using a known concentration of a standard.

According to various embodiments, a method for relative quantitation of one or more catecholamine analytes can comprise labeling the one or more analytes, followed by analysis using mass spectrometry. According to some embodiments the one or more catecholamine analytes and/or salts or hydrates thereof can be quantified. As discussed herein, the label can be a 4-aminoantipyrine reagent or a heavy atom derivative thereof. The labeling can be performed according to the reaction conditions described herein.

It should be understood that absolute quantitation of catecholamine analytes, where the standard has a known concentration of a catecholamine analyte, can be performed in the same manner as described above for relative quantitation. Also, where catecholamine analytes and/or salts or hydrates of catecholamine analytes are mentioned above, it should be understood that any catecholamine analyte can be used.

According to various embodiments, samples containing one or more catecholamines may be enriched by various methods prior to analysis. The enrichment method can depend upon the type of sample, such as blood (fresh or dried), plasma, serum, urine, or saliva. Exemplary enrichment methods can comprise, without limitation, protein precipitation, liquid-liquid extraction, solid-liquid extraction, affinity capture/release, antibody mediated enrichment and ultrafiltration. Other enrichment methods, or a combination of two or more enrichment methods may be used. The sample can be any type of sample suitable for analysis, such as, but not limited to, as blood (fresh or dried), plasma, serum, urine, or saliva.

In some embodiments, the analysis of catecholamine analytes can comprise generating reporter ions, e.g., via a high-energy collision in a mass spectrometer, and utilizing the intensity or the peak area of the reporter ions for quantitation. By way of example, the adducts shown above can undergo neutral loss during high energy collisions (MSMS) leaving a charged analyte species as the reporter ion, and the reporter ion can then be subjected to $MS^3$ analysis. In some embodiments, the adducts can generate a tag fragment upon a high energy collision, and the tag fragment can then be subjected to MS³ analysis. Examples of the tag fragments are shown as a compound of Formula III.

As described herein, the analytes of the standard and sample can be mixed together and analyzed to determine the concentration of the analytes in the sample. The analysis can comprise separating the mixture to form separated analytes, and analyzing the separated analytes. Methods of separation that can be used include gas chromatographic methods, liquid chromatographic methods, other chromatographic methods, electrophoretic methods, electroosmotic methods, mass differential separation methods, and the like. In an exemplary embodiment, liquid chromatography is used to separate the various analytes in the mixture and thus form separated analytes.

In some embodiments, chromatographic separation can be performed on a reversed phase column and peaks eluting from the column can be subjected to subsequent analysis. In some embodiments, the subsequent analysis can comprise mass spectrometry or, more particularly, Parent Daughter Ion Transition Monitoring (PDITM). By comparing the results from the PDITM, the concentration of the catecholamine analyte in the sample can be determined, as is described in more detail below. More details about PDITM and its use can be found in published application US 2006/0183238 A1, which is incorporated herein in its entirety by reference.
m Different liquid chromatography and mass spectrometry methods, systems, and software that can be used in accordance with various embodiments of the present teachings include those described in U.S. Provisional Patent Application No. 61/182,748 filed May 31, 2009, and in U.S. Patent Application No. US 2006/0183238 A1 which published on Aug. 17, 2006. Both of these references are incorporated herein by reference.

Aspects of the present teachings can be further understood in light of the following examples, which should not be construed as limiting the scope for the present teachings in any way.

EXAMPLES

Example 1

To a 0.5 mL solution of dopamine hydrochloride (1 mg/mL) and 4-Aminoantipyrine (4-AAP, 1 mg/mL) in 100 mM ammonium bicarbonate buffer (pH 8-9) a solution (0.1 mL, 0.25 mg/mL in water) of $K_2[Fe(CN)_6]$ was added and mixed. The purple solution so produced was filtered through a C18 (500 mg) cartridge and analyzed by MS/MS. The reaction produced the following adduct according to the following scheme:

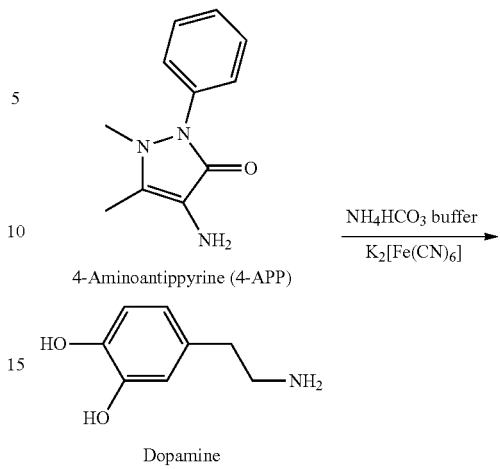

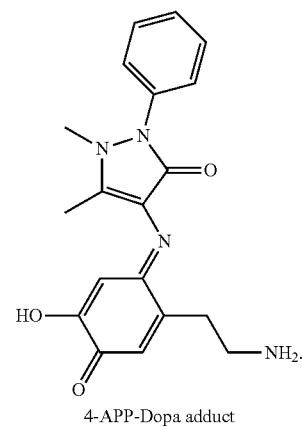

All chemicals were purchased form Sigma Aldrich. The reaction involves addition of 4-AAP and $K_2[Fe(CN)_6]$ aqueous solutions to an ammonium bicarbonate buffered dopamine solution and vortexing for 5 min. at ambient temperature when purple color 4-AAP-Dopa adduct formed. After desalting through a C18 cartridge, the product was analyzed for parent and daughter ions in an QTRAP® 5500 mass-spectrometer using direct infusion mode.

The Parent ion was observed at m/z 353.1 (MH+) and after fragmentation daughter ions are observed at m/z=150.5, 159.5, 187.5, 202.8 (intense), 204.7 (intense), 324.9 and 336.0. All of these transitions can be used for MRM monitoring. One structure specific fragment was identified as (observed mass=204.7)

27

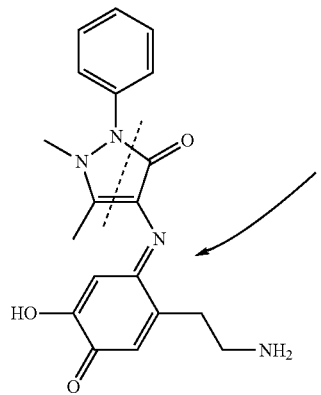

Chemical Formula: $C_{10}H_9N_2O_3{}^3$
Exact Mass: 205.06

Figure 2:
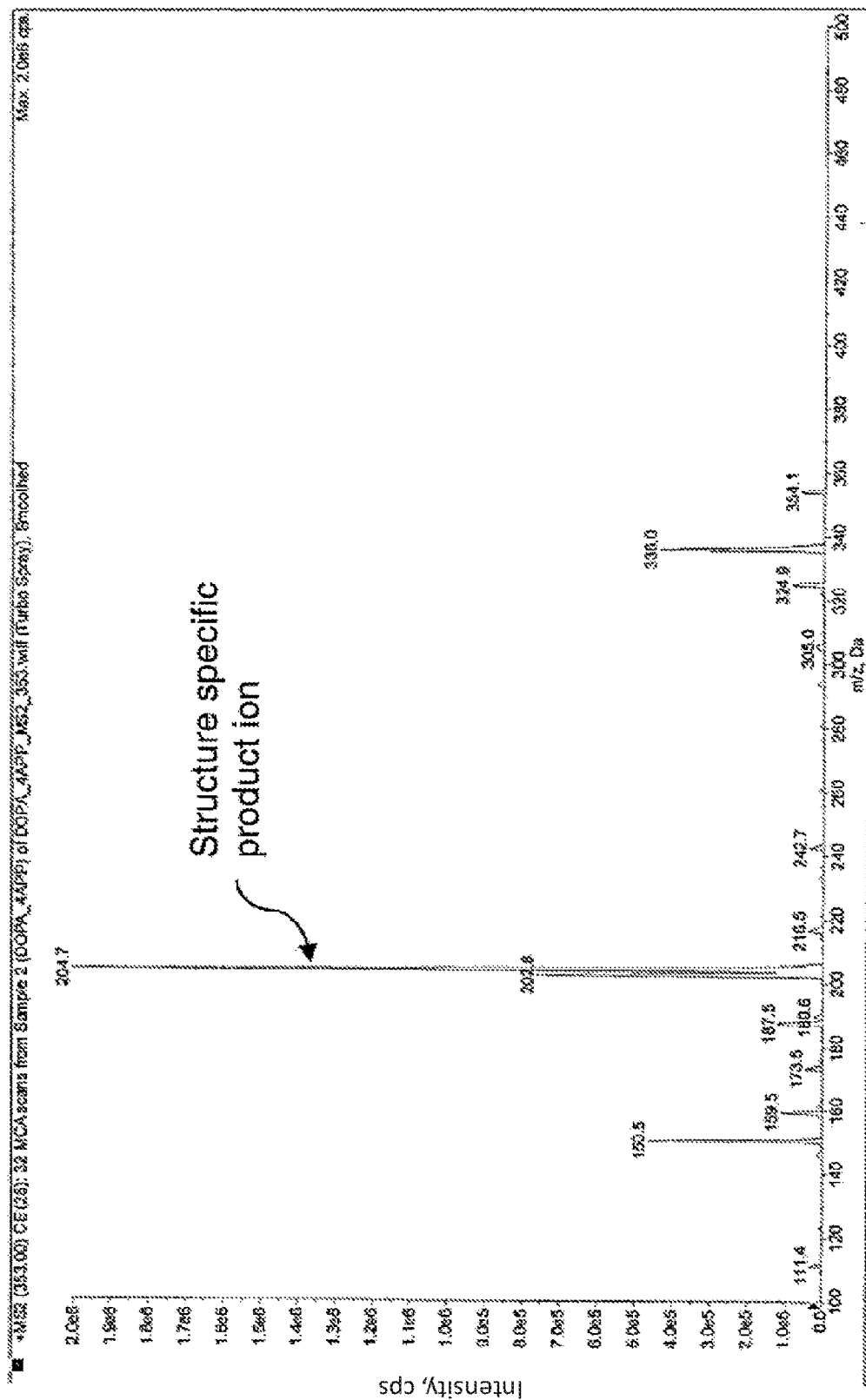
FIG. 2 shows the MSMS scan of the 4-AAP-dopamine adduct daughter ions that was generated according to Example 1.

FIGS. 1 and 2 show spectra that identify the species.

The section headings used herein are for organizational purposes only and are not to be construed as limiting the subject matter described in any way.

While the applicant's teachings are described in conjunction with various embodiments, it is not intended that the applicant's teachings be limited to such embodiments. On the contrary, the applicant's teachings encompass various alternatives, modifications, and equivalents, as will be appreciated by those of skill in the art.

While the above description provides examples and specific details of various embodiments, it will be appreciated that some features and/or functions of the described embodiments admit to modification without departing from the scope of the described embodiments. The above description is intended to be illustrative of the invention, the scope of which is limited only by the language of the claims appended hereto. Other embodiments of the present teachings will be apparent to those skilled in the art from consideration of the present specification and practice of the present teachings disclosed herein. It is intended that the present specification and examples be considered exemplary only.

The invention claimed is:

1. A method of detecting the presence of one or more catecholamines in a sample, the method comprising:

a) reacting the sample with a 4-aminoantipyrine reagent, or a heavy atom derivative thereof, under conditions sufficient to react with a catecholamine, if any, present in the sample to form a 4-aminoantipyrine-reagent-catecholamine adduct, or a heavy atom derivative thereof;

b) obtaining a mass spectrum of said reacted sample; and c) analyzing the mass spectrum to determine whether the sample contains a 4-aminoantipyrine-reagent-catecholamine adduct or an ionic fragment thereof, wherein the 4-aminoantipyrine reagent is a compound of Formula I or a heavy atom derivative thereof:

28

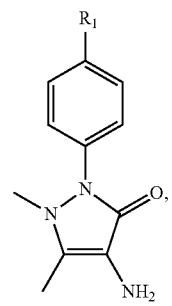

I wherein $R^1$

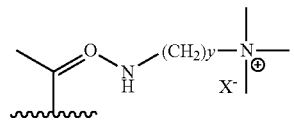

y is 1-6; and

X is an anion.

2. The method of claim 1, wherein the one or more catecholamines is epinephrine, isoprenaline, norepinephrine, nordefrin, adrenalone hydrochloride, epinine hydrochloride, 2-(dimethylamino)-3',4'-dihydroxy-(8Cl), 2-(Dimethylamino)-3',4'-dihydroxyacetophenone, dioxethedrin, etyprenaline, N-methylepinephrine, dihydroxyephedrine hydrochloride, butylnoradrenaline, ethylnoradrenaline, 3,4-dihydroxy-phenylalanine, dopamine, or a salt or hydrates thereof, or any combination thereof.

3. The method of claim 1, wherein the analyzing step comprises detecting one or more mass signals associated with any of said adduct and one or more fragments thereof and quantitating the amount of the catecholamine in the sample.

4. The method of claim 1, wherein the heavy atom derivative of Formula I is a compound of Formula Ia, Ib, or Ic.

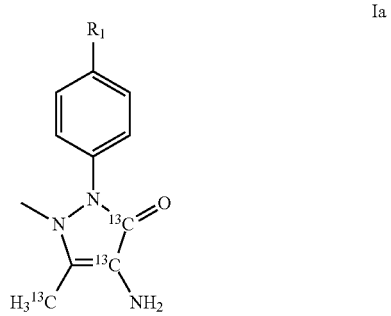

Ia

-continued

Ib

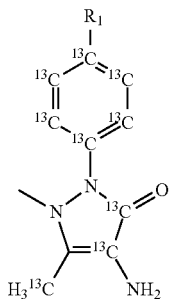

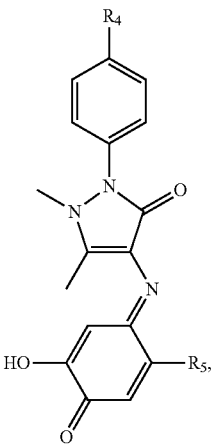

II wherein

R<sub>4</sub> is H or

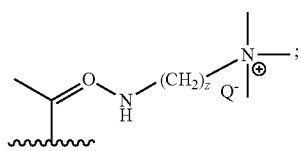

Ic

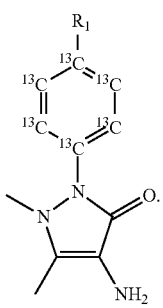

R<sub>5</sub> is

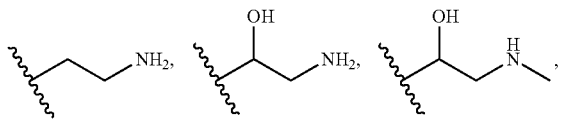

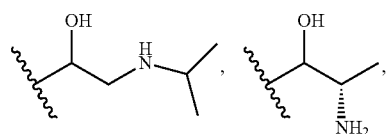

5. A method of detecting the presence of one or more catecholamines in a sample, the method comprising:

a) reacting the sample with a 4-aminoantipyrine reagent, or a heavy atom derivative thereof, under conditions sufficient to react with a catecholamine, if any, present in the sample to form a 4-aminoantipyrine-reagent-catecholamine adduct, or a heavy atom derivative thereof;

b) obtaining a mass spectrum of said reacted sample; and c) analyzing the mass spectrum to determine whether the sample contains a 4-aminoantipyrine-reagent-catecholamine adduct or an ionic fragment thereof, wherein the aminoantipyrine-catecholamine adduct is a compound of Formula II, or a heavy atom derivative thereof:

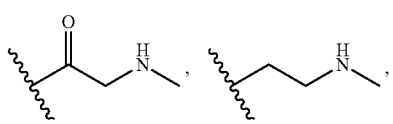

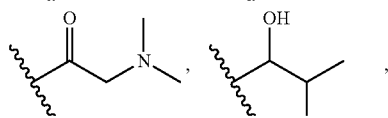

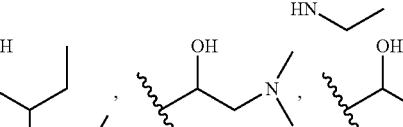

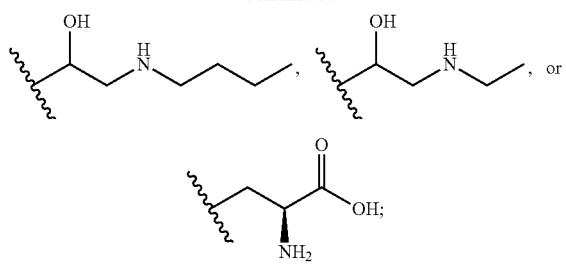

, or z is 1-6; and

Q is a halogen.

6. The method of claim 5, wherein the heavy atom derivative of Formula II is a compound of Formula IIa or IIb

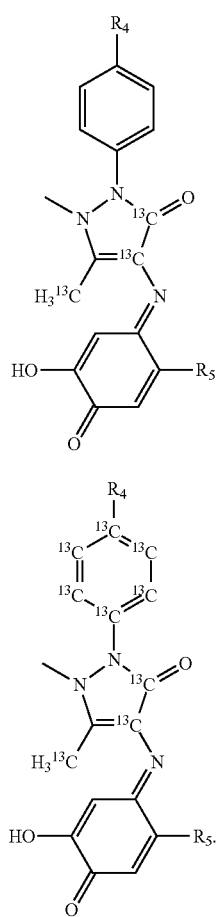

7. The method of claim 5, wherein the ionic fragment of the aminoantipyrine-catecholamine adduct is a compound of Formula III, or a heavy atom derivative thereof:

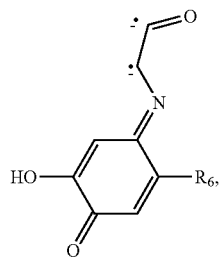

wherein
$R_6$ is

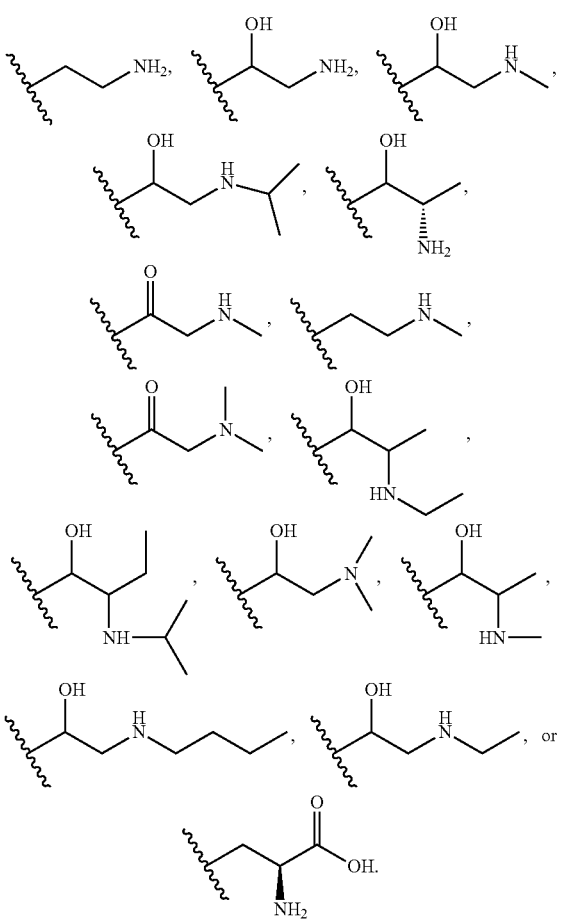

8. The method of claim 1, wherein reacting the sample with 4-aminoantipyrine under conditions to form a 4-aminoantipyrine-catecholamine adduct comprises contacting the sample with 4-aminoantipyrine in the presence of ammonium bicarbonate and $K_2[Fe(CN)_6]$ to produce the 4-aminoantipyrine-catecholamine adduct.

* * * * *